(12) United States Patent
Koch

(10) Patent No.: US 6,718,973 B2
(45) Date of Patent: Apr. 13, 2004

(54) EVAPORATION CHAMBER FOR A RESPIRATORY GAS HUMIDIFIER

(75) Inventor: Jochim Koch, Ratzeburg (DE)

(73) Assignee: Dräger Medical AG & Co. KGaA, Lübeck (DE)

(*) Notice: Subject to any disclaimer, the term of this patent is extended or adjusted under 35 U.S.C. 154(b) by 195 days.

(21) Appl. No.: 09/916,290

(22) Filed: Jul. 30, 2001

(65) Prior Publication Data
US 2002/0017298 A1 Feb. 14, 2002

(30) Foreign Application Priority Data
Aug. 5, 2000 (DE) .......................... 100 38 365

(51) Int. Cl.[7] .............................. A61M 15/00
(52) U.S. Cl. .................. 128/203.16; 128/203.26; 261/DIG. 65; 454/241
(58) Field of Search ................ 454/141, 142, 454/237, 241, 251–253; 128/204.18, 207.14–207.18, 201.13, 203.12, 203.16, 203.17, 204.17, 203.26; 261/DIG. 65

(56) References Cited

U.S. PATENT DOCUMENTS

| | | | | | |
|---|---|---|---|---|---|
| 4,060,576 A | * | 11/1977 | Grant | ...................... | 261/130 |
| 4,201,204 A | * | 5/1980 | Rinne et al. | ........... | 128/203.27 |
| 5,329,939 A | * | 7/1994 | Howe | ..................... | 128/203.27 |
| 5,373,841 A | * | 12/1994 | Kyllonen et al. | ...... | 128/203.18 |
| 5,699,983 A | * | 12/1997 | Ellsworth | ................ | 244/118.5 |
| 5,916,493 A | * | 6/1999 | Miller | ........................ | 261/154 |
| 5,943,473 A | * | 8/1999 | Levine | ....................... | 392/401 |

* cited by examiner

Primary Examiner—Glenn K. Dawson
(74) Attorney, Agent, or Firm—Walter Ottesen

(57) ABSTRACT

An evaporator chamber for mixing water vapor with respiratory gas has a supply opening for the respiratory gas, an inlet opening for the water vapor and an outlet opening for the humidified respiratory gas. With the evaporator chamber, an excellent mixing is achieved with the smallest possible structural volume. The evaporator chamber is configured as a hollow body (1) having an essentially circularly-shaped inner wall surface (5). The supply opening (4) on the upper end of the hollow body (1) is arranged in a manner which conducts in the respiratory gas essentially tangentially to the inner wall surface (5). The outlet opening (6) is located at the lower end of the hollow body (1) and the inlet opening (9) lies between the supply opening (4) and the outlet opening (6).

7 Claims, 1 Drawing Sheet

EVAPORATION CHAMBER FOR A RESPIRATORY GAS HUMIDIFIER

BACKGROUND OF THE INVENTION

An evaporator chamber is disclosed in German patent publication DE-GM 9,307,380. An evaporator chamber housing is provided with a deflection surface for guiding the respiratory gas flow and is connected to a boiling chamber for generating water vapor. The water vapor enters the evaporator chamber housing arranged above the boiling chamber and condenses, in part, on the deflection surfaces. The respiratory gas is deflected multiple times within the evaporator chamber housing by deflecting surfaces and is enriched with the water vapor.

It is disadvantageous with respect to this known evaporation chamber that a relatively large structural volume is needed because of the multiple deflection in order to arrive at an optimal through mixing and that the through-flow resistance is clearly increased because of the deflecting surfaces. This operates disadvantageously on a possible spontaneous breathing activity of the patient. Furthermore, considerable heat is outputted to the ambient because of the evaporator chamber housing since the deflecting surfaces act as heat exchanger elements. The heat output reduces the respiratory gas temperature.

A respiratory humidifier is disclosed in U.S. Pat. No. 6,102,037 wherein superheated water vapor is fed into a tube system conducting respiratory gas. This vapor is to be mixed with dry cold respiratory gas from a ventilating apparatus so that a physiologically humidified and warmed ventilating air is supplied to the patient. The known respiratory gas humidifier is based on the physical principle that the metering of the water quantity takes place proportionally to the amount of the respiratory gas flow while considering a thermodynamic mixture equation. When, for example, the metering of the water quantity is too low or the supplied respiratory gas is too high, then the desired humidifying temperature is not reached. A temperature measurement directly rearward of the respiratory gas humidifier supplies a representative quantity for the correct metering of the water quantity. With the aid of the thermodynamic compensation computation, a determination can be made as to how much the water metering must be increased so that the humidifying temperature increases to the desired temperature. When the humidifying temperature corresponds to the desired temperature, then the precomputed water quantity has also been vaporized. The same applies in the reverse case when the water quantity is too high or the respiratory gas flow is too low.

A good mixing of the dry cold respiratory gas with the hot vapor is therefore a precondition so that the temperature, which is measured at one point with a temperature sensor directly behind the respiratory gas humidifier, corresponds to the mean temperature in the cross section of the humidified and warmed respiratory gas.

If one conducts a hot vapor flow into a cold dry respiratory gas flow, then an excellent mixing is still not ensured. The two flows can continue to run unmixed parallel to each other and this is greatly dependent upon the flow conditions and flow velocities.

In the case of the intermittent ventilation, an additional difficulty is that the flow conditions are not constant but change periodically. A respiratory gas flow is supplied during the inhalation and practically no respiratory gas flow is present during exhalation. In the known respiratory gas humidifier, the supplied vapor would collect in the tube system during the exhalation phase and the air would heat intensely and oversaturate.

SUMMARY OF THE INVENTION

It is an object of the invention to improve an evaporator chamber of the kind described above wherein an excellent mixing is achieved with the smallest possible structural volume.

The evaporator chamber of the invention is for mixing water vapor with a respiratory gas. The evaporator chamber includes: a hollow body having a wall defining an inner wall surface having an essentially circular shape; the hollow body having an upper end and a lower end; the hollow body having a supply opening through which the respiratory gas is supplied essentially tangentially to the inner wall surface; the hollow body further having an inlet opening for water vapor which mixes with the respiratory gas to form a humidified respirator gas; an outlet opening through which the humidified respiratory gas flows out of the hollow body; and, the supply opening being mounted at the upper end so that the outlet opening is disposed at the lower end and so that the inlet opening is arranged between the supply opening and the outlet opening.

The advantage of the invention is essentially that the supply of the dry respiratory gas into the evaporator chamber takes place tangentially to the interior wall surface and above the inlet opening for the water vapor. Condensate which is possibly present can flow off via the outlet opening located at the lower end. With the tangential feed of the respiratory gas into the evaporator chamber, the dry respiratory gas is conducted precisely into the interior wall region where the hot vapor has collected during the exhalation phase. With the exhalation of the patient, the respiratory gas flow is interrupted so that the hot vapor can rise. Interior surfaces, which are warmed and on which condensate has possibly collected are flushed with each inhalation phase by the respiratory gas at high flow velocity so that these walls are again dried and cooled down.

The evaporator chamber is configured to be cylindrical so that a circular movement is imparted to the inflowing respiratory gas to provide an excellent mixing with the water vapor. The evaporator chamber can be produced as a disposable part and can, for example, be made of polycarbonate or polyethylene. The evaporator chamber can be, for example, made of polysulphone if the evaporator chamber is to be reusable and sterilizable. The evaporator chamber can be placed in a washing machine for cleaning the same or can be flushed under a water stream.

The tube or hose connections of the evaporator chamber have standardized conical connections depending upon the application, for ventilating adults or for ventilating newborns.

The evaporator chamber is advantageously so configured that the water vapor is fed centrally. In addition to an excellent mixing, this affords the advantage that the respiratory gas flows directly along the inner wall surface and has only slight contact with the superheated water vapor.

A first temperature sensor is advantageously mounted in a supply channel extending in the upward flow direction of the supply opening. With this temperature sensor, the temperature of the gas, which flows into the evaporator chamber, is measured. The first temperature sensor is so mounted that it is located below the inlet opening for the water vapor so that the temperature measurement is not affected by the temperature of the water vapor. With an interruption of the respiratory gas flow (for example, during the exhalation), the water vapor first collects at the upper end of the evaporator chamber. Even for a longer respiratory gas interruption, the vapor cloud would expand slowly downwardly but would not reach the first temperature sensor. This is important for the reason that the temperature of the inflowing cold respiratory gas is needed in the thermodynamic computation of the required hot vapor temperature. An entry temperature, which is made incorrect by the water vapor, would lead to the situation that the hot vapor of the ventilating humidifier would be controlled to too low a temperature. As a consequence, the water quantity increases which leads to an unwanted collection of condensate in the hose system behind the evaporator chamber. The evaporator chamber is therefore so configured that the first temperature sensor is at the same elevation or below the inlet opening for the superheated water vapor. The volume within the evaporator chamber is so dimensioned that, even for longer exhalation times, the water vapor cloud can be stored within the evaporator chamber.

The outlet opening of the evaporator chamber is located at the lower end thereof so that possibly occurring condensate can flow away directly out of the evaporator chamber.

A flow nozzle is provided in the region of the outlet opening and this flow nozzle constricts the flow channel. This leads to the condition that a so-called dead water region with intense swirling is formed behind the flow nozzle. This wanted swirling leads to a further excellent mixing with the hot vapor. The flow resistance of this nozzle is so selected that it is less than one millibar for a respiratory gas flow of 60 liters per minute.

A second temperature sensor is arranged in an outlet channel which follows the outlet opening. This second sensor measures the temperature of the humidified respiratory gas. The second temperature sensor is located in a region where water vapor condensation can arise. For this reason, this sensor would measure too low a temperature when coated with water. According to the invention, the second temperature sensor is therefore shielded with a baffle plate so that it lies in the flow shadow of the baffle plate.

Very different flow velocities are present at the second temperature sensor during the inhalation and exhalation in the intermitting respiratory gas flow. The time-dependent trace of the temperature, which is measured with a very rapidly measuring temperature sensor having a very low mass, would have a periodic component. The real mass of the utilized second temperature sensor operates as a time-dependent lowpass filter so that the temperature determined therefrom yields a mean value of the periodic trace under the precondition that the thermal conditions in the flow cross section are symmetrical and evenly distributed.

BRIEF DESCRIPTION OF THE DRAWING

The invention will now be described with respect to the single FIGURE (FIG. 1) of the drawing which schematically shows an evaporator chamber in accordance with an embodiment of the invention.

DESCRIPTION OF THE PREFERRED EMBODIMENTS OF THE INVENTION

Figure 1:
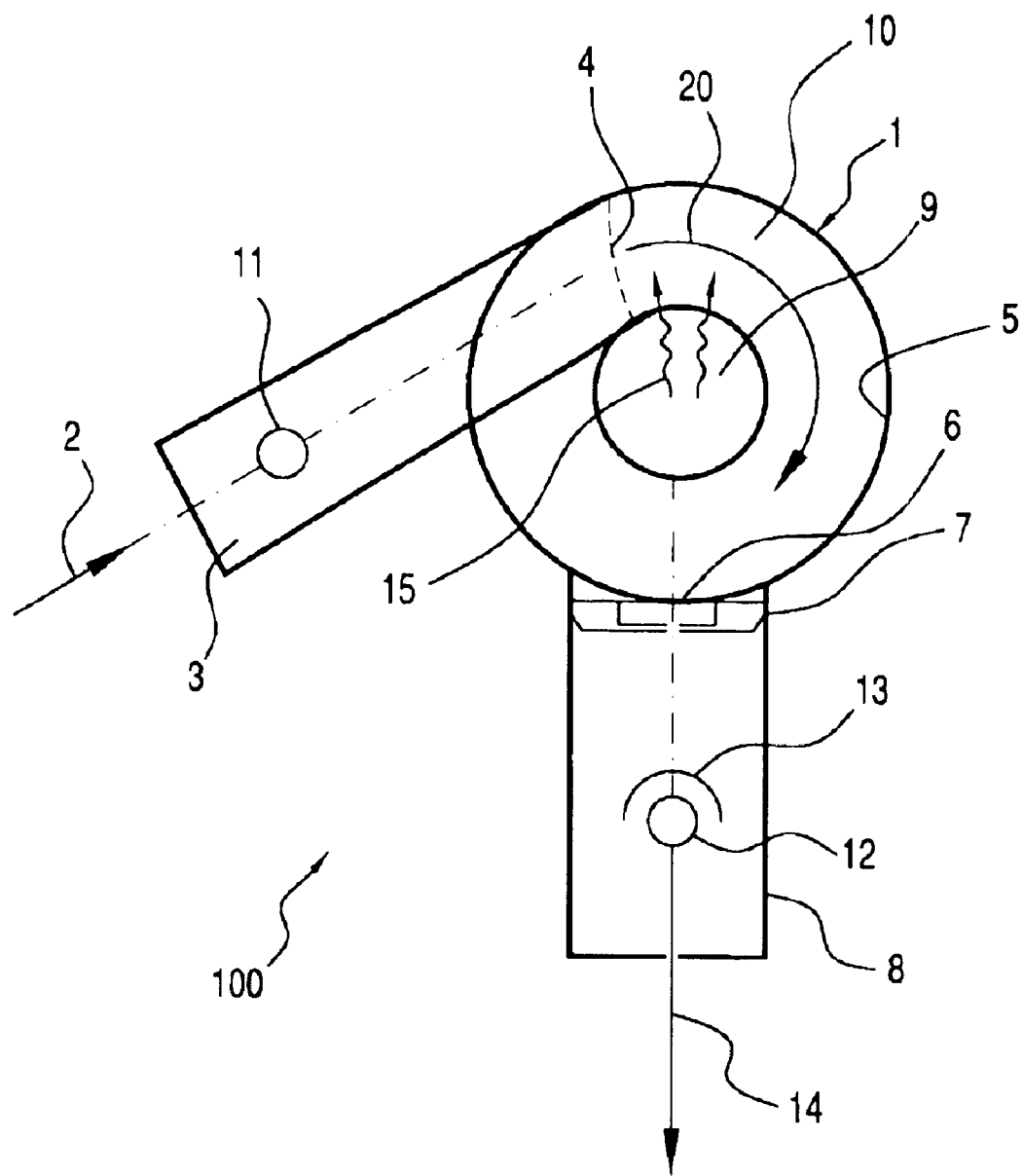

Reference numeral 100 identifies an evaporator chamber in accordance with the invention wherein respiratory gas flows in the direction of arrow 2 via a supply channel and through an inlet opening 4 into a cylindrical hollow body 1. The inlet opening 4 is shown schematically by a broken line. The respiratory gas is deflected at an internal wall surface 5 having a circular shape as shown schematically by flow line 20 and leaves the hollow body 1 via an outlet opening 6, a flow nozzle 7 and an outlet channel 8.

An inlet opening 9 for the superheated water vapor is formed in a side wall of the cylindrical hollow body 1 and is located in the region of a center point surrounded by the circularly-shaped inner wall surface 5. Referred to the inlet opening 9, the supply channel 3 is so arranged that the respiratory gas flows tangentially into the evaporator chamber 100 as indicated by flow line 20 and above the inlet opening 9. The water vapor moves upwardly from inlet opening 9 as indicated by flow line 15 and collects first in a space 10 in the region of the supply opening 4 and mixes there directly with the respiratory gas flow. A first temperature sensor 11 is located in the supply channel 3 for measuring the temperature of the respiratory gas flowing into the hollow body 1. The first temperature sensor 11 is so mounted that it lies below the inlet opening 9 so that no water vapor reaches the first temperature sensor 11 and falsifies the temperature measurement during time intervals in which no respiratory gas flows into the hollow body 1, for example, during the exhalation phase of the patient. A second temperature sensor 12 measures the temperature of the humidified respiratory gas and is located in the outlet channel 8. The second temperature sensor 12 is arranged in the flow shadow of a baffle plate 13 and is thereby protected against condensate drops. The gas exit of the humidified respiratory gas at the end of the outlet channel 8 is indicated by arrow 14.

It is understood that the foregoing description is that of the preferred embodiments of the invention and that various changes and modifications may be made thereto without departing from the spirit and scope of the invention as defined in the appended claims.

What is claimed is:

1. An evaporator chamber for mixing water vapor with a respiratory gas, the evaporator chamber comprising:

a hollow body having a wall defining an inner wall surface having an essentially cylindrical shape;

said hollow body having an upper end and a lower end;

said hollow body having a supply opening through which the respiratory gas is supplied essentially tangentially to said inner wall surface;

said hollow body further having an inlet opening for water vapor which mixes in said hollow body with said respiratory gas to form a humidified respiratory gas;

an outlet opening disposed at said lower end through which said humidified respiratory gas flows out of said hollow body; and, said supply opening being mounted at said upper end so that said outlet opening is disposed at said lower end and so that said inlet opening is arranged between said supply opening and said outlet opening.

2. The evaporator chamber of claim 1, wherein said inlet opening for said water vapor lies in the region of a center point enclosed by said cylindrically-shaped inner wall surface.

3. The evaporator chamber of claim 1, further comprising: a supply channel for conducting said respiratory gas to said supply opening; and, a first temperature sensor mounted in said supply channel upstream of said supply opening.

4. The evaporator chamber of claim 3, wherein said first temperature sensor is mounted at the same elevation as said inlet opening for said water vapor.

5. The evaporator chamber of claim 3, wherein said first temperature sensor is mounted at an elevation below said inlet opening for said water vapor.

6. The evaporator chamber of claim 3, further comprising:

an outlet channel for conducting said humidified respiratory gas away from said outlet opening;

a second temperature sensor mounted in said outlet channel; and, a baffle plate for shielding said second temperature sensor with respect to condensate.

7. The evaporator chamber of claim 1, further comprising a flow nozzle mounted in the region of said outlet opening.

* * * * *